(12) United States Patent
White et al.

(10) Patent No.: US 9,790,156 B2
(45) Date of Patent: Oct. 17, 2017

(54) OLEFIN HYDROFORMYLATION METHODS FOR OBTAINING BRANCHED ALDEHYDES

(71) Applicant: Lyondell Chemical Technology, L.P., Houston, TX (US)

(72) Inventors: Daniel F. White, Houston, TX (US); Beaven S. Mandimutsira, Sugar Land, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/340,389

(22) Filed: Nov. 1, 2016

(65) Prior Publication Data

US 2017/0121262 A1     May 4, 2017

Related U.S. Application Data

(60) Provisional application No. 62/250,892, filed on Nov. 4, 2015.

(51) Int. Cl.
    *C07C 45/49*     (2006.01)
    *C07C 45/50*     (2006.01)
    *B01J 31/24*     (2006.01)

(52) U.S. Cl.
    CPC ......... *C07C 45/505* (2013.01); *B01J 31/2409* (2013.01); *C07C 45/49* (2013.01); *B01J 2231/321* (2013.01); *B01J 2531/822* (2013.01)

(58) Field of Classification Search
    CPC ..... C07C 45/49; C07C 45/505; B01J 2231/00
    See application file for complete search history.

(56) References Cited

U.S. PATENT DOCUMENTS

| | | | | |
|---|---|---|---|---|
| 5,693,832 | A * | 12/1997 | Fujita | ...................... C07C 45/49 549/475 |
| 6,225,509 | B1 * | 5/2001 | Dubner | ................... C07C 45/49 568/451 |
| 7,271,295 | B1 | 9/2007 | White et al. | |
| 7,279,606 | B1 | 10/2007 | White | |
| 7,294,602 | B1 | 11/2007 | White | |

OTHER PUBLICATIONS

N. A. Hassan et al, Journal of Heterocyclic Chemistry, vol. 44, No. 4, Jul. 1, 2007, pp. 775-782, XP55054157, ISSN:0022-152X, DOI:10.1002/jhet.5570440404.
T. Saito et al, Advanced Synthesis & Catalysis, vol. 343, No. 3, 2001, pp. 264-267, XP002765915.
M. Kranenburg et al., Organometallics, American Chemical Society, US, vol. 14, No. 6, Jun. 1, 1995, pp. 3081-3089, XP000565303, ISSN:0276-7333, DOI:10.1021/OM00006A057.
The International Search Report and Written Opinion for PCT/US2016/059936 dated Jan. 27, 2017.

\* cited by examiner

*Primary Examiner* — Sikarl Witherspoon

(57) ABSTRACT

The present technology relates to methods of hydroformylating allyl alcohol to 4-hydroxybutanal and 2-methyl-3-hydroxypropanal, comprising (i) admixing allyl alcohol with CO and $H_2$ to form a starting material mixture, and (ii) reacting the starting material mixture in the presence of a catalyst under conditions capable of forming a product mixture comprising 4-hydroxybutanal and 2-methyl-3-hydroxypropanal, wherein the catalyst is a transition metal complex comprising a transition metal ion and a diphosphine ligand with a bite angle from about 70° to about 100°, and wherein the ratio of 4-hydroxybutanal to 2-methyl-3-hydroxypropanal in the product mixture is less than 1.5:1.

19 Claims, 1 Drawing Sheet

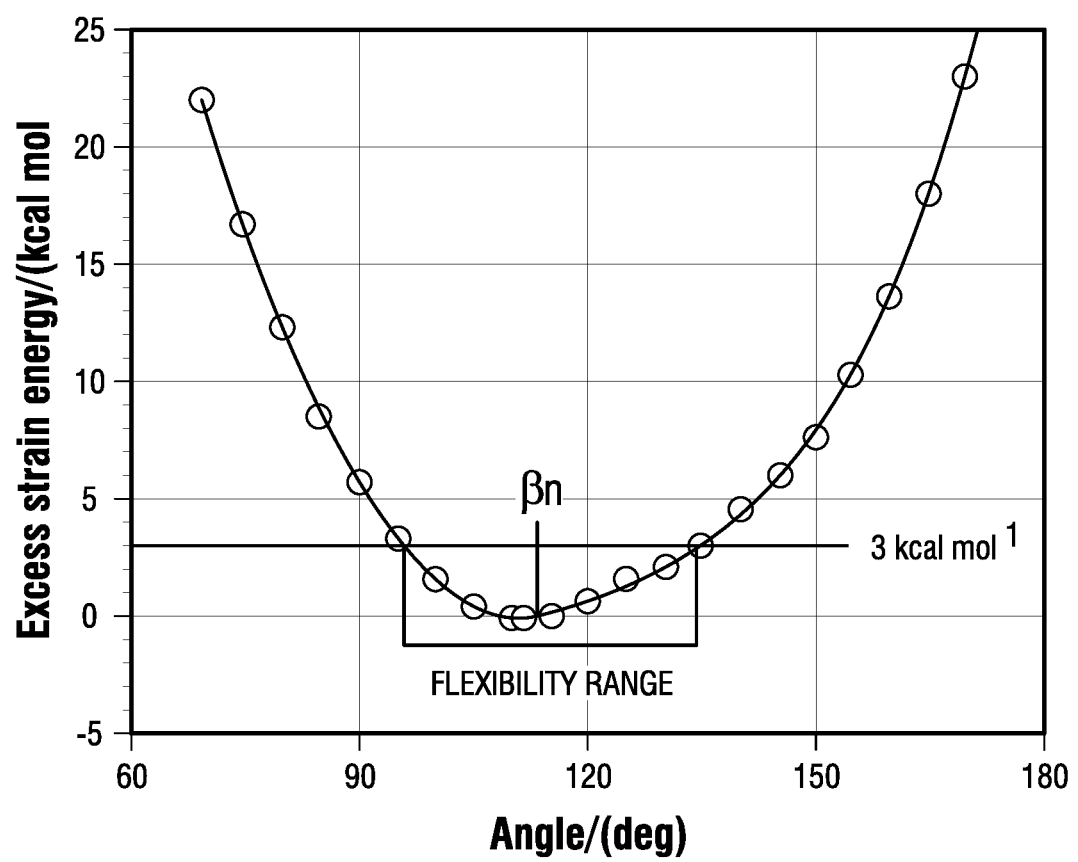

OLEFIN HYDROFORMYLATION METHODS FOR OBTAINING BRANCHED ALDEHYDES

CROSS-REFERENCE TO RELATED APPLICATIONS

This application claims the benefit of priority to U.S. Provisional Application No. 62/250,892, filed on Nov. 4, 2015, which is incorporated herein by reference in its entirety.

FIELD OF THE INVENTION

The present disclosure relates to catalysts, catalyst compositions, and methods for the hydroformylation of olefins.

DESCRIPTION OF RELATED ART

Hydroformylation is used as an industrial process for the production of aldehydes from olefins. This process uses homogeneous catalysts to add a formyl group (CHO) and a hydrogen atom across a carbon-carbon double bond of the olefin. In addition to unsubstituted olefins, substituted olefins such as allyl alcohol, acrylic acid, and methacrylic acid can also be hydroformylated. Numerous research efforts have been undertaken to optimize the production of the ratio of linear to branched hydroformylation reaction products. In the past, many of the catalyst optimizations have focused on increasing the amount of the linear products. However, the branched products are also useful, and thus catalysts which result in a higher branched to linear reaction product ratio would be benefit in order to better address this need.

SUMMARY OF THE INVENTION

In one aspect, the present disclosure provides methods comprising the steps:
(i) admixing allyl alcohol with CO and $H_2$ to form a starting material mixture; and
(ii) reacting the starting material mixture in the presence of a catalyst under conditions capable of forming a product mixture comprising 4-hydroxybutanal and 2-methyl-3-hydroxypropanal;
wherein the catalyst is a transition metal complex comprising a transition metal ion and a diphosphine ligand with a bite angle from about 70° to about 100°, and wherein the ratio of 4-hydroxybutanal to 2-methyl-3-hydroxypropanal in the product mixture is less than 1.5:1.

In some embodiments, the diphosphine ligand has a bite angle from about 85° to about 95°.

In some embodiments, the ratio of 4-hydroxybutanal to 2-methyl-3-hydroxypropanal is less than 0.75:1.

In some embodiments, the transition metal is a Rh, Re, or Co ion, for example, a Rh ion.

In some embodiments, the reaction of step (ii) occurs at a temperature from about 20° C. to about 120° C. and at a pressure from about 20 psi to about 600 psi (about 140 to about 4,100 kPa).

In some embodiments, the starting material mixture further comprises a solvent.

In some embodiments, the amount of allyl alcohol in the starting material mixture is 5-40 wt %. In some embodiments, the starting material mixture further comprises a $phosphine_{(C3-30)}$ or a substituted $phosphine_{(C3-30)}$.

In some embodiments, the methods further comprise a step (iii): separating 2-methyl-3-hydroxypropanal from the product mixture to obtain purified 2-methyl-3-hydroxypropanal.

In some embodiments, the methods further comprise a step (iv): hydrogenating the product mixture in the presence of $H_2$ gas and a hydrogenation catalyst to produce a diol.

In some embodiments, the diphosphine ligand has the formula:

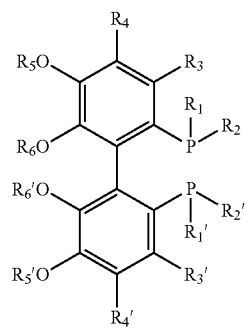

wherein:
$R_1$, $R_2$, $R_1'$, and $R_2'$ are each independently selected from $aryl_{(C6-12)}$ or substituted $aryl_{(C6-12)}$;
$R_3$, $R_4$, $R_3'$, and $R_4'$ are each independently selected from hydrogen, $alkyl_{(C1-12)}$, substituted $alkyl_{(C1-12)}$, $aryl_{(C6-12)}$, or substituted $aryl_{(C6-12)}$;
$R_5$ is $alkyl_{(C1-12)}$, substituted $alkyl_{(C1-12)}$, $aryl_{(C6-12)}$, or substituted $aryl_{(C6-12)}$; or is taken together with $R_6$ and is $alkanediyl_{(C1-6)}$ or substituted $alkanediyl_{(C1-6)}$;
$R_5'$ is $alkyl_{(C1-12)}$, substituted $alkyl_{(C1-12)}$, $aryl_{(C6-12)}$, or substituted $aryl_{(C6-12)}$; or is taken together with $R_6'$ and is $alkanediyl_{(C1-6)}$ or substituted $alkanediyl_{(C1-6)}$;
$R_6$ is $alkyl_{(C1-12)}$, substituted $alkyl_{(C1-12)}$, $aryl_{(C6-12)}$, or substituted $aryl_{(C6-12)}$; is taken together with $R_5$ and is $alkanediyl_{(C1-6)}$ or substituted $alkanediyl_{(C1-6)}$; or is taken together with $R_6'$ and is $alkanediyl_{(C1-6)}$ or substituted $alkanediyl_{(C1-6)}$; and
$R_6'$ is $alkyl_{(C1-12)}$, substituted $alkyl_{(C1-12)}$, $aryl_{(C6-12)}$, or substituted $aryl_{(C6-12)}$; is taken together with $R_5'$ and is $alkanediyl_{(C1-6)}$ or substituted $alkanediyl_{(C1-6)}$; or is taken together with $R_6$ and is $alkanediyl_{(C1-6)}$ or substituted $alkanediyl_{(C1-6)}$.

In some embodiments, the diphosphine ligand is selected from those described above or below. For example, in some of these embodiments, the diphosphine ligand is further defined as:

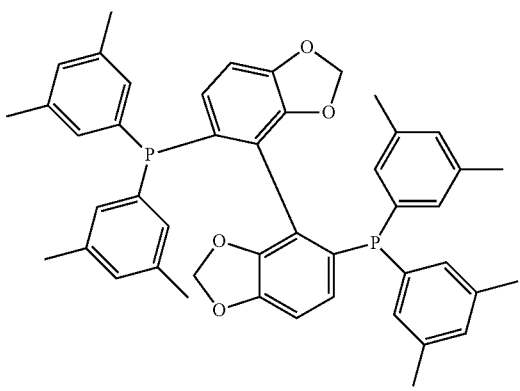

In some embodiments, the catalyst is present in the product mixture in an amount from about 10 ppm to about 1,000 ppm.

In some embodiments, the reaction time of step (ii) is from about 0.5 hours to about 4 hours.

In some embodiments, the methods result in an HMPA yield greater than 50%. In some embodiments, the methods result in an allyl alcohol conversion percentage of greater than 75%.

In another aspect, hydroformylation methods are provided comprising:
  (i) admixing an α-olefin$_{(C3-24)}$, a substituted α-olefin$_{(C3-24)}$, or styrene with CO and H$_2$ to form a starting material mixture; and
  (ii) reacting the starting material mixture in the presence of a catalyst under conditions capable of producing linear and branched aldehydes,
wherein the catalyst is a transition metal complex comprising a transition metal ion and a diphosphine ligand with a bite angle from about 70° to about 100°, and wherein the ratio of the linear to branched aldehydes is less than 1.5:1.

In some embodiments, the α-olefin$_{(C3-24)}$ or substituted α-olefin$_{(C3-24)}$ is hexene, allyl alcohol, allyl acetate, or vinyl acetate. In some embodiments, the diphosphine ligand is selected from those described above or below.

While multiple embodiments are disclosed, still other embodiments will become apparent to those skilled in the art from the following detailed description. As will be apparent, certain embodiments, as disclosed herein, are capable of modifications in various aspects without departing from the spirit and scope of the claims as presented herein. Accordingly, the drawings and detailed description are to be regarded as illustrative in nature and not restrictive.

DESCRIPTION OF THE DRAWING

The following FIGURES illustrate various embodiments of the subject matter disclosed herein. The claimed subject matter may be better understood by the following description taken in conjunction with the accompanying FIGURE, in which:

The FIGURE shows the bite angle (βn) of bidentate phosphorus ligands as a function of excess strain energy (kcal/mol). The flexibility range indicated on this graph shows were the potential energy is 3 kcal/mol or lower.

DETAILED DESCRIPTION OF THE INVENTION

I. Hydroformylation Reactions

In one aspect, hydroformylation methods are provided comprising:
  (i) admixing an α-olefin$_{(C3-24)}$, a substituted α-olefin$_{(C3-24)}$, or styrene with CO and H$_2$ to form a starting material mixture; and
  (ii) reacting the starting material mixture in the presence of a catalyst under conditions capable of producing linear and branched aldehydes,
wherein the catalyst is a transition metal complex comprising a transition metal ion and a diphosphine ligand with a bite angle from about 70° to about 100°, and wherein the ratio of the linear to branched aldehydes is less than 1.5:1. In some embodiments, the α-olefin$_{(C3-24)}$ or substituted α-olefin$_{(C3-24)}$ is hexene, allyl alcohol, allyl acetate, or vinyl acetate.

In another aspect, the present disclosure provides methods comprising the steps:

(i) admixing allyl alcohol with CO and H$_2$ to form a starting material mixture; and
  (ii) reacting the starting material mixture in the presence of a catalyst under conditions capable of forming a product mixture comprising 4-hydroxybutanal and 2-methyl-3-hydroxypropanal;
wherein the catalyst is a transition metal complex comprising a transition metal ion and a diphosphine ligand with a bite angle from about 70° to about 100°, and wherein the ratio of 4-hydroxybutanal to 2-methyl-3-hydroxypropanal in the product mixture is less than 1.5:1.

A. Catalyst Compositions

In some embodiments, the catalyst is a transition metal complex comprising a transition metal ion and a diphosphine ligand with a bite angle from about 70° to about 100°. In some of these embodiments, the diphosphine ligand has a bite angle from about 75° to about 95°, from about 85° to about 100°, or from about 85° to about 95°.

In some embodiments, the transition metal is a rhodium (Rh), rhenium (Re) or cobalt (Co) ion. In some embodiments, the diphosphine ligand has the formula:

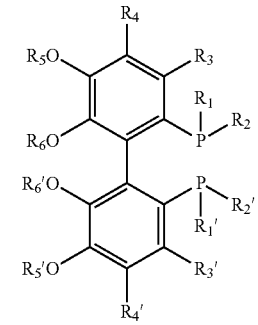

wherein:
  $R_1$, $R_2$, $R_1'$, and $R_2'$ are each independently selected from aryl$_{(C6-12)}$ or substituted aryl$_{(C6-12)}$;
  $R_3$, $R_4$, $R_3'$, and $R_4'$ are each independently selected from hydrogen, alkyl$_{(C1-12)}$, substituted alkyl$_{(C1-12)}$, aryl$_{(C6-12)}$, or substituted aryl$_{(C6-12)}$;
  $R_5$ is alkyl$_{(C1-12)}$, substituted alkyl$_{(C1-12)}$, aryl$_{(C6-12)}$, or substituted aryl$_{(C6-12)}$; or is taken together with $R_6$ and is alkanediyl$_{(C1-6)}$ or substituted alkanediyl$_{(C1-6)}$;
  $R_5'$ is alkyl$_{(C1-12)}$, substituted alkyl$_{(C1-12)}$, aryl$_{(C6-12)}$, or substituted aryl$_{(C6-12)}$; or is taken together with $R_6'$ and is alkanediyl$_{(C1-6)}$ or substituted alkanediyl$_{(C1-6)}$;
  $R_6$ is alkyl$_{(C1-12)}$, substituted alkyl$_{(C1-12)}$, aryl$_{(C6-12)}$, or substituted aryl$_{(C6-12)}$; is taken together with $R_5$ and is alkanediyl$_{(C1-6)}$ or substituted alkanediyl$_{(C1-6)}$; or is taken together with $R_6'$ and is alkanediyl$_{(C1-6)}$ or substituted alkanediyl$_{(C1-6)}$; and
  $R_6'$ is alkyl$_{(C1-12)}$, substituted alkyl$_{(C1-12)}$, aryl$_{(C6-12)}$, or substituted aryl$_{(C6-12)}$; is taken together with $R_5'$ and is alkanediyl$_{(C1-6)}$ or substituted alkanediyl$_{(C1-6)}$; or is taken together with $R_6$ and is alkanediyl$_{(C1-6)}$ or substituted alkanediyl$_{(C1-6)}$.

In some of these embodiments, the diphosphine ligand is further defined as:

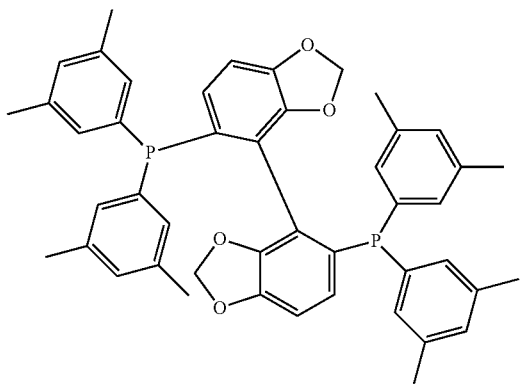

In some embodiments, the starting material mixture further comprises a phosphine$_{(C3-30)}$ or a substituted phosphine$_{(C3-30)}$.

B. Reaction Conditions

In some embodiments, the methods provided herein comprising reacting the starting material mixtures defined above in the presence of a catalyst under conditions capable of forming product mixtures comprising linear and branched aldehydes, including, for example, 4-hydroxybutanal and 2-methyl-3-hydroxypropanal.

In some embodiments, the starting material mixture further comprises a solvent. In some embodiments, the solvent is an organic solvent, for example, with low water content. In some of these embodiments, the solvent is a hydrocarbon, for example, an aromatic solvent (e.g., toluene), an alcohol, an ether (e.g., MTBE), or an aliphatic hydrocarbon (e.g., cyclohexane). In some embodiments, the amount of allyl alcohol in the starting material mixture is 5-40 wt %. In some of these embodiments, the amount of allyl alcohol in the starting material mixture is 5-25 wt % or 10-25 wt %.

In some embodiments, the catalyst is a transition metal complex comprising a transition metal ion and a diphosphine ligand with a bite angle from about 70° to about 100°. In some of these embodiments, the transition metal ion is a Rh, Re, or Co ion, for example, a Rh ion. In some of these embodiments, the transition metal ion is present in the starting material mixture or in the product mixture in an amount of from 10 ppm to 1,000 ppm, in an amount from 50 ppm to 500 ppm, or in an amount from 100 ppm to 200 ppm.

In some embodiments, the reaction of step (ii) occurs at a temperature from about 20° C. to about 120° C. and at a pressure from about 20 psi to about 600 psi (about 140 to about 4,100 kPa). In some embodiments, the temperature is from 20° C. to 120° C., from 45° C. to 85° C., or from 50° C. to 80° C. In some embodiments, the temperature is about 80° C. In some embodiments, the pressure is from 20 psi to 600 psi, from 30 psi to 400 psi, from 30 psi to 300 psi. In some embodiments, the pressure is about 200 psi. In some embodiments, the pressure of the CO is from 5 to 100 psi. In some embodiments, the pressure of the hydrogen is from 40 psi to 200 psi. In some embodiments, the molar ratio of H$_2$:CO is from 10:1 to 1:10, from 3:1 to 1:3, or about 1:1. In some embodiments, the reaction time of step (ii) is from about 0.5 hours to about 4 hours.

In some embodiments, the methods further comprise a step (iii) of separating 2-methyl-3-hydroxypropanal from the product mixture to obtain purified 2-methyl-3-hydroxypropanal. In some embodiments, the ratio of 4-hydroxybutanal to 2-methyl-3-hydroxypropanal is less than 1.5:1, less than 1:1, or less than 0.75:1.

In some embodiments, the methods further comprise a step (iv) of hydrogenating the product mixture in the presence of H$_2$ gas and a hydrogenation catalyst to produce a diol. In some embodiments, the hydrogenation catalyst is a transition metal or transition metal alloy. In some embodiments, the transition metal is nickel (Ni), Co, Ru, platinum (Pt), palladium (Pd), copper (Cu), zinc (Zn), or chromium (Cr). In some embodiments, the hydrogenation catalyst is an alloy of these. In some embodiments, the hydrogenation catalyst is Ni, for example, Raney®-Nickel. In some embodiments, the hydrogenation reaction is carried out under a hydrogen pressure from 200 psi to 1,000 psi or from 300 to 1,000 psi. In some embodiments, the hydrogenation reaction is carried out at a temperature from 60° C. to 200° C. or from 80° C. to 140° C. In some embodiments, the reaction time of step (iv) is from about 1 hour to about 10 hours.

In some embodiments, the methods result in an HMPA yield greater than 50%, greater than 60%, or a value in a range of from 60-99.9%. In some embodiments, the methods result in an allyl alcohol conversion percentage of greater than 75%, greater than 85%, or greater than 99.5%.

U.S. Pat. Nos. 7,271,295, 7,279,606, and 7,294,602 provide additional information regarding hydroformylation reaction conditions, procedures, equipment, substrates, products, and catalysts. Content from these references is incorporated by reference herein in its entirety.

II. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012), which is incorporated herein by reference.

III. Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the variation of error for the device, the method being employed to determine the value, or the variation that exists among the studies.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two and may be compared with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are synonymous.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH₃ (Me), —CH₂CH₃ (Et), —CH₂CH₂CH₃ (n-Pr or propyl), —CH(CH₃)₂ (i-Pr, ⁱPr or isopropyl), —CH₂CH₂CH₂CH₃ (n-Bu), —CH(CH₃)CH₂CH₃ (sec-butyl), —CH₂CH(CH₃)₂ (isobutyl), —C(CH₃)₃ (tert-butyl, t-butyl, t-Bu or ᵗBu), and —CH₂C(CH₃)₃ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH₂— (methylene), —CH₂CH₂—, —CH₂C(CH₃)₂CH₂—, and —CH₂CH₂CH₂— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "cycloalkyl" when used without the "substituted" modifier refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include —CH(CH₂)₂ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include —CH=CH₂ (vinyl), —CH=CHCH₃, —CH=CHCH₂CH₃, —CH₂CH=CH₂ (allyl), —CH₂CH=CHCH₃, and —CH=CHCH=CH₂. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH₃)CH₂—, —CH=CHCH₂—, and —CH₂CH=CHCH₂— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are exclusively carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are exclusively carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

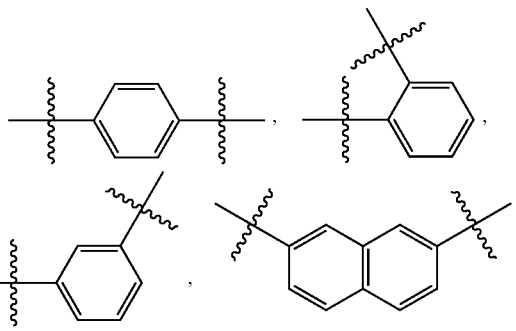

-continued

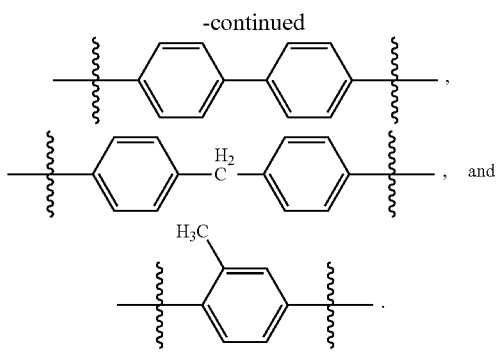
, and

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O) CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

As used herein, "average molecular weight" refers to the weight average molecular weight (Mw) as determined by gel permeation chromatography (GPC).

As used in the context of application, the term "bite angle" is measured as described in Casey et al. (1992), which is incorporated herein by reference, and may alternatively be referred to as the "natural bite angle" or "βn". While in no way limiting the scope of the present technology, a large bite angle may stabilize the intermediate(s) formed during a hydroformylation, while metal complexes such as those described in the present disclosure may demonstrate an increase in the rate of catalysis where ligands with larger bite angles are employed. Ligands and considerations for utilizing the same may be made as described in Dierkes et al., *J. Chem. Soc., Dalton Trans.* 10, 1519-1530 (1999), which is incorporated herein by reference, while reaction conditions for use in the present technology are disclosed in Casey et al. and Dierkes et al. as well as Kranenburg et al., *Organometallics* 14, 3081-3089 (1995), which is incorporated herein by reference.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing exclusively those one or more steps and also covers other unlisted steps.

The "conversion" or "yield" is the amount of product produced relative to the amount of starting materials added to the reaction mixture and is given as a percentage. In some cases, the conversion or yield includes the total amount of both the linear and the branched product produced in a given reaction.

HBA is an abbreviation for 4-hydroxybutanal.

HMPA is an abbreviation for 2-methyl-3-hydroxypropanal.

The term "ligand flexibility" is measured using a potential energy diagram can then be drawn by fixing the bite angle at various values by applying a large bending force constant and calculating the strain energy at those values including by using a potential energy diagram such as the one in the FIGURE. The flexibility range is determined from the potential energy diagram by taking the available bite angles within a 3 kcal mol$^{-1}$ excess strain energy range. This method has been correlated with bite angles determined through X-ray crystallography, and the correlation was found to be strong.

The "linear to branched" ratio, which is also expressed as "linear:branched", "1:b", or "N:I", is the ratio of the amount of linear product to the amount of branched product.

A "method" is series of one or more steps undertaking lead to a final product, result or outcome. As used herein, the word "method" is used interchangeably with the word "process".

The terms "phosphine" and "phosphane" are used synonymously herein. When used without the "substituted" modifier these terms refer to a compound of the formula PR$_3$, wherein each R is independently hydrogen, alkyl, cycloalkyl, alkenyl, aryl, or aralkyl, as those terms are defined above. Non-limiting examples include PMe$_3$, PPh$_3$, and PCy$_3$ (tricyclohexylphosphine). The terms "trialkylphosphine" and "trialkylphosphane" are also synonymous. Such groups are a subset of phosphine, wherein each R is an alkyl group.

The term "diphosphine" refers to any of the following:

A compound of the formula R$_2$—P-L-P—R$_2$, wherein each R is independently hydrogen, alkyl, cycloalkyl, alkenyl, aryl, or aralkyl, and wherein L is alkanediyl, cycloalkanediyl, alkenediyl, or arenediyl. Optionally, one or more hydrogen atom attached to a carbon atom may be independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

A compound shown in Table 1.

A compound of the formula:

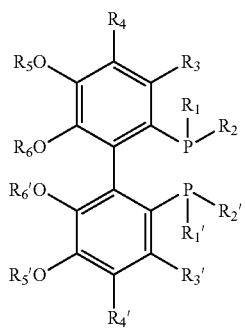

wherein:
R$_1$, R$_2$, R$_1$', and R$_2$' are each independently aryl$_{(C6-12)}$ or substituted aryl$_{(C6-12)}$;
R$_3$, R$_4$, R$_3$', and R$_4$' are each independently hydrogen, alkyl$_{(C1-12)}$, substituted alkyl$_{(C1-12)}$, aryl$_{(C6-12)}$, or substituted aryl$_{(C6-12)}$;
R$_5$ is alkyl$_{(C1-12)}$, substituted alkyl$_{(C1-12)}$, aryl$_{(C6-12)}$, or substituted aryl$_{(C6-12)}$; or is taken together with R$_6$ and is alkanediyl$_{(C1-6)}$ or substituted alkanediyl$_{(C1-6)}$;
R$_5$' is alkyl$_{(C1-12)}$, substituted alkyl$_{(C1-12)}$, aryl$_{(C6-12)}$, or substituted aryl$_{(C6-12)}$; or is taken together with R$_6$' and is alkanediyl$_{(C1-6)}$ or substituted alkanediyl$_{(C1-6)}$;
R$_6$ is alkyl$_{(C1-12)}$, substituted alkyl$_{(C1-12)}$, aryl$_{(C6-12)}$, or substituted aryl$_{(C6-12)}$; is taken together with R$_5$ and is alkanediyl$_{(C1-6)}$ or substituted alkanediyl$_{(C1-6)}$; or is taken together with R$_6$' and is alkanediyl$_{(C1-6)}$ or substituted alkanediyl$_{(C1-6)}$; and
R$_6$' is alkyl$_{(C1-12)}$, substituted alkyl$_{(C1-12)}$, aryl$_{(C6-12)}$, or substituted aryl$_{(C6-12)}$; is taken together with R$_5$' and is alkanediyl$_{(C1-6)}$ or substituted alkanediyl$_{(C1-6)}$; or is taken together with R$_6$ and is alkanediyl$_{(C1-6)}$ or substituted alkanediyl$_{(C1-6)}$.

The term "transition metal" is used to describe a metal atom such as a metal cation selected from elements in columns 3-12 on the periodic table inclusive of the lanthanide and actinide groups of metals. The transition metals that may be used herein include elements from columns 7-9 on the period table. In some embodiments, the transition metal is manganese (Mn), Re, Fe, ruthenium (Ru), osmium (Os), Co, Rh, or iridium (Ir).

The above definitions supersede any conflicting definition in any reference that is incorporated by reference herein. The fact that certain terms are defined, however, should not be considered as indicative that any term that is undefined is indefinite. Rather, the terms used are believed to describe the appended claims such that one of ordinary skill can appreciate the breadth and scope of the technology.

EXAMPLES

The following examples are included to demonstrate embodiments of the appended claims. Those of skill in the art should appreciate that many changes can be made in the specific embodiments which are disclosed and still obtain a like or similar result without departing from the spirit and scope of the disclosure herein.

Example 1

Methods and Materials i. Hydroformylation Conditions

The hydroformylation experiments were carried out in anhydrous toluene with the stoichiometry determined by the amount of Rh. In a typical experiment, a rhodium complex (1 equivalent, 4.3×10$^{-5}$ moles) was added to this solution of dry degassed toluene (15 g) and the desired phosphine ligand. This solution was then transferred to a 50 mL Parr autoclave. The autoclave was then flushed three times with a 1:1 CO/H$_2$ mixture, and pressurized to 180 psi (1240 kPa), and the autoclave was heated with stirring, to the indicated temperature, for example 80° C. Once the desired temperature was stably attained for at least 5 minutes, allyl alcohol (3.5 mL) was then injected and the autoclave pressure increased to 200 psi (1,379 kPa) with the CO:H$_2$ mixture. The reactor was then maintained at a constant 200 psi (1,379 kPa) pressure and the gas uptake with time was monitored until there was no further gas uptake. The reactor was cooled down, depressurized and the solution was analyzed by gas chromatography to determine the products of the reaction, which included HBA, MHPA and C$_3$ products, (n-propanol and Propionaldehyde). Results are shown in Tables 2 and 4.

ii. Ligands

TABLE 1

Diphosphine Ligands for Hydroformylation Reactions

| Ligand Name | Ligand Formula or Chemical Name |
|---|---|
| NORPHOS | 2,3-Bis(diphenylphosphino)bicyclo[2.2.1]hept-5-ene |
| dppe | 1,2-Bis(diphenylphosphino)ethane |
| dppp or dpp(propane) | 1,3-Bis(diphenylphosphino)propane |
| RDM-SegPhos | 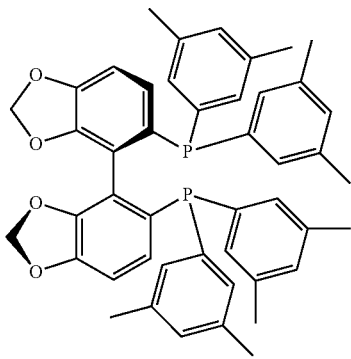 |
| BIPHEP | 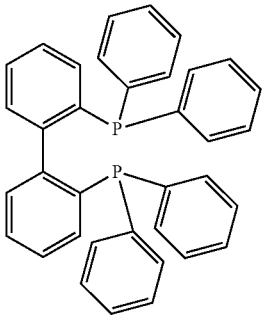 [SMILES: c1ccc(P(c2ccccc2)c2ccccc2-c2ccccc2P(c2ccccc2)c2ccccc2)cc1] |
| BINAP | 2,2'-Bis(diphenylphosphino)-1,1'-binaphthalene |
| dppBz or dpp(benzene) | 1,2-Bis(diphenylphosphanyl)benzene |
| DPPPS | 2,2-Dimethyl-[1,3,2]-dioxasilolane-4,5-dicarboxylic acid dimethyl ester |
| 1,7-DPP-NAP | 1,7-Bis(diphenylphosphino)naphthalene |
| R-Tol-SDP | (R)-(+)-7,7'-Bis[di(4-methylphenyl)phosphino]-2,2',3,3'-tetrahydro-1,1'-spirobiindene, (R)-7,7'-Bis[di(p-methylphenyl)phosphino]-1,1'-spirobiindane |
| R-SDP | (R)-(+)-7,7'-Bis(diphenylphosphino)-2,2',3,3'-tetrahydro-1,1'-spirobiindene, (R)-7,7'-Bis(diphenylphosphino)-1,1'-spirobiindane |
| CTH-BINAM | 2,2'-Bis(N-diphenylphosphinoamino)-5,5',6,6',7,7',8,8'-octahydro-1,1'-binaphthyl |

TABLE 1-continued

Diphosphine Ligands for Hydroformylation Reactions

| Ligand Name | Ligand Formula or Chemical Name |
|---|---|
| S-C6-TunePhos | 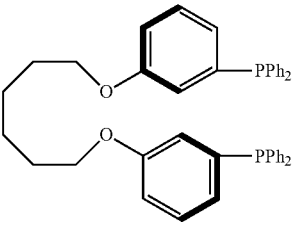 |
|  | 1,16-bis(diphenylphosphino)-6,7,8,9,10,11-hexahydrodibenzo[b,d][1,6]dioxacyclododecine |
| dpp(hexane) | 1,6-Bis(diphenylphosphino)hexane |
| TXP | Tri-(3,5-dimethylphenyl)phosphine |
| cis-1,4-DPPCyH | cis-1,4-Bis(diphenylphosphinomethyl)cyclohexane |
| TTP | Tri-(4-methylphenyl)phosphine |
| PhanePhos | Bis(diphenylphosphino)-[2.2]-paracyclophane |
| RMeO-BIPHEP | 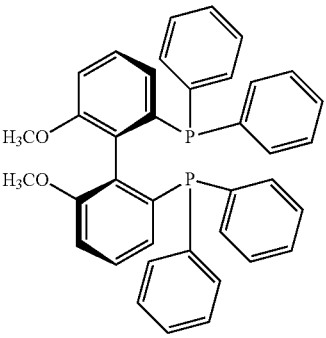 |
| R-SEGPHOS | 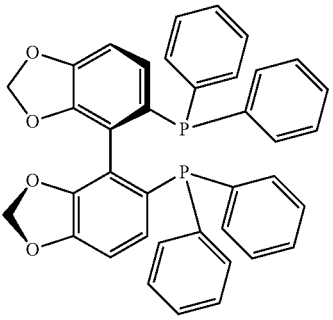 |
| DTBM-SEGPHOS | 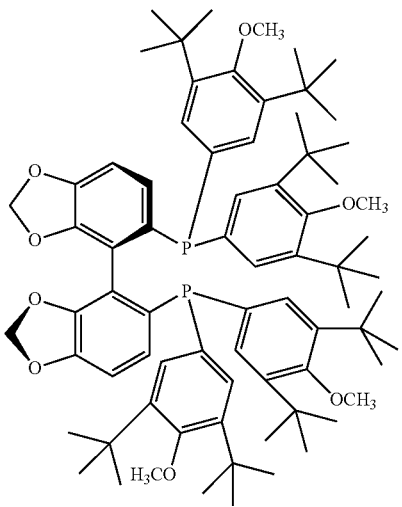 |
| R-C3-TUNEPHOS | (R)-1,13-Bis(diphenylphosphino)-7,8-dihydro-6H-dibenzo[f,h][1,5]dioxonin |
| (R)-DM-SEGPHOS® | (R)-(+)-5,5'-Bis[di(3,5-xylyl)phosphino]-4,4'-bi-1,3-benzodioxole, [(4R)-(4,4'-bi-1,3-benzodioxole)-5,5'-diyl]bis[bis(3,5-dimethylphenyl)phosphine] |

Example 2

Hydroformylation Reaction Using Ligand

The results of the hydroformylation reaction with allyl alcohol are shown in Table 2. Ligands which exhibited a bite angle of less than 100° showed an increased preference for the branched hydroformylation product. In addition, an increased amount of HMPA (2-methyl-3-hydroxypropanal) relative to HBA (4-hydroxybutanal) was produced for the ligands with a bite angle of less than 100°. Additional hydroformylation results are shown in Table 3.

TABLE 2

Hydroformylation Reaction Products and Properties for Various Diphosphine Ligands

| Ligand | βn (°) | Flexibility (°) | L:B | % Yield of HBA | % Yield of HMPA | % Total Conversion |
|---|---|---|---|---|---|---|
| NORPHOS | 89.8 | 80-100 (20) | 0.29 | 8.41 | 29.35 | 38.05 |
| dppe | 77.2 | 67-94 (27) | 0.34 | 8.46 | 25.17 | 33.97 |
| dpp(propane) | 88.1 | 76-106 (30) | 0.35 | 11.72 | 33.87 | 45.94 |
| (R)-DM-SEGPHOS® | 94 |  | 0.52 | 34.4 | 65.09 | 100.01 |
| BIPHEP | 93 | 77-110 (33) | 0.58 | 10.37 | 18.02 | 28.97 |
| BINAP | 94.1 | 78-111 (33) | 0.74 | 13.83 | 18.83 | 33.4 |
| dpp(benzene) | 79.8 | 71-93 (22) | 1.1 | 12.21 | 11.07 | 24.38 |
| DPPPS | 99.1 | 85-115 (30) | 1.26 | 45.82 | 36.43 | 83.51 |
| 1,7-DPP-NAP |  |  | 1.28 | 37.57 | 29.07 | 67.92 |
| R-Tol-SDP |  |  | 1.38 | 51.16 | 36.78 | 89.32 |
| R-SDP |  |  | 1.42 | 50.36 | 35.3 | 87.08 |
| CTH-BINAM |  |  | 1.49 | 25.96 | 17.43 | 44.88 |
| S-C6-TunePhos |  |  | 1.58 | 54.99 | 34.7 | 91.27 |

TABLE 2-continued

Hydroformylation Reaction Products and Properties for Various Diphosphine Ligands

| Ligand | βn (°) | Flexibility (°) | L:B | % Yield of HBA | % Yield of HMPA | % Total Conversion |
|---|---|---|---|---|---|---|
| dpp(hexane) | 120.6 | 100-161 (61) | 1.62 | 60.75 | 37.64 | 100.01 |
| TXP | N/A | N/A | 1.69 | 62.95 | 36.94 | 101.58 |
| cis-1,4-DPPCyH | 132.4 | | 1.73 | 63.32 | 36.47 | 101.52 |
| TTP | N/A | N/A | 1.84 | 64.69 | 35.17 | 101.7 |
| PhanePhos | 118.5 | 95-134 (39) | 1.86 | 63.79 | 34.79 | 100.44 |
| TPP | N/A | N/A | 1.92 | 65.83 | 34.03 | 101.78 |

TABLE 3

Allyl Alcohol Hydroformylation Reaction Product Results

| | Rh Source 4.3e−5 Moles | Ligand 1 Diphosphine 8.6e−5 Moles | HBA mol % | HMPA mol % | C3 mol % | L:B Ratio mol % | AA Conv % |
|---|---|---|---|---|---|---|---|
| C1 | Rh(CO)$_2$acac | BIPHEP | 57.9 | 36 | 5.4 | 1.61 | 99.72 |
| R1 | Rh(CO)$_2$acac | RMeO-BIPHEP | 30.2 | 45.9 | 0.83 | 0.66 | 77.54 |
| R2 | Rh(CO)$_2$acac | R-SEGPHOS | 41.5 | 50.7 | 3.67 | 0.82 | 96.12 |
| R3 | Rh(CO)$_2$acac | DM-SEGPHOS | 26.9 | 48.5 | 0.8 | 0.55 | 76.6 |
| R4 | Rh(CO)$_2$acac | DTBM-SEGPHOS | 16.6 | 36.6 | 0.76 | 0.45 | 54.21 |
| R5 | Rh(CO)$_2$acac | R-C$_3$-TUNEPHOS | 30.6 | 48.8 | 0.52 | 0.63 | 80.04 |

All of the compounds, complexes, and methods disclosed and claimed herein can be made and executed without undue experimentation in light of the present disclosure. While the compounds, complexes, and methods of this disclosure have been described in terms of certain embodiments, it will be apparent to those of skill in the art that variations may be applied to the compounds, complexes, and methods, as well as in the steps or in the sequence of steps of the method described herein without departing from the concept, spirit, and scope of the appended claims. More specifically, it will be apparent that certain compounds which are chemically related may be substituted for the compounds described herein while the same or similar results would be achieved. Similar substitutes and modifications apparent to those skilled in the art are deemed to be within the spirit, scope and concept of the present disclosure as defined by the appended claims.

REFERENCES

The following references to the extent that they provide exemplary procedural or other details supplementary to those set forth herein, are specifically incorporated herein by reference.

U.S. Pat. No. 7,271,295
U.S. Pat. No. 7,294,602
U.S. Pat. No. 7,279,606
Anderson, N. G., *Practical Process Research & Development—A Guide For Organic Chemists*, 2$^{nd}$ ed., Academic Press, New York, 2012.
Casey, et al., *J. Am. Chem. Soc.*, 114(14):5535-43, (1992)
Dierkes et al., *J. Chem. Soc., Dalton Trans.*, 10: 1519-1530 (1999)
Van Leeuwen, et al., *Tetrahedron: Asymmetry*, 4:1625 (1993)

What is claimed is:

1. A method comprising:
  (i) admixing allyl alcohol with CO and H$_2$ to form a starting material mixture; and
  (ii) reacting the starting material mixture in the presence of a catalyst under conditions capable of forming a product mixture comprising 4-hydroxybutanal and 2-methyl-3-hydroxypropanal;
  wherein the catalyst is a transition metal complex comprising a transition metal ion and a diphosphine ligand with a bite angle from about 70° to about 100°, and wherein the ratio of 4-hydroxybutanal to 2-methyl-3-hydroxypropanal in the product mixture is less than 1.5:1.

2. The method of claim 1, wherein the diphosphine ligand has a bite angle from about 85° to about 95°.

3. The method of claim 1, wherein the ratio of 4-hydroxybutanal to 2-methyl-3-hydroxypropanal is less than 0.75:1.

4. The method of claim 1, wherein the transition metal is a Rh, Re, or Co ion.

5. The method of claim 4, wherein the transition metal ion is a Rh ion.

6. The method of claim 1, wherein the reaction of step (ii) occurs at a temperature from about 20° C. to about 120° C. and at a pressure from about 20 psi to about 600 psi (about 140 to about 4,100 kPa).

7. The method of claim 1, wherein the starting material mixture further comprises a solvent.

8. The method of claim 7, wherein the amount of allyl alcohol in the starting material mixture is 5-40 wt %.

9. The method of claim 1, wherein the starting material mixture further comprises a phosphine$_{(C3-30)}$ or a substituted phosphine$_{(C3-30)}$.

10. The method of claim 1, further comprising:
  (iii) separating 2-methyl-3-hydroxypropanal from the product mixture to obtain purified 2-methyl-3-hydroxypropanal.

11. The method of claim 1, further comprising:
(iv) hydrogenating the product mixture in the presence of H$_2$ gas and a hydrogenation catalyst to produce a diol.

12. The method of claim 1, wherein the diphosphine ligand has the formula:

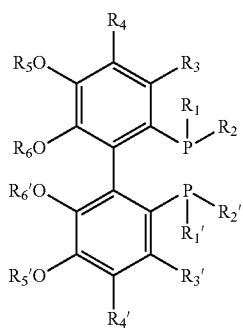

wherein:
- R$_1$, R$_2$, R$_1$', and R$_2$' are each independently selected from aryl$_{(C6-12)}$ or substituted aryl$_{(C6-12)}$;
- R$_3$, R$_4$, R$_3$', and R$_4$' are each independently selected from hydrogen, alkyl$_{(C1-12)}$, substituted alkyl$_{(C1-12)}$, aryl$_{(C6-12)}$, or substituted aryl$_{(C6-12)}$;
- R$_5$ is alkyl$_{(C1-12)}$, substituted alkyl$_{(C1-12)}$, aryl$_{(C6-12)}$, or substituted aryl$_{(C6-12)}$; or is taken together with R$_6$' and is alkanediyl$_{(C1-6)}$ or substituted alkanediyl$_{(C1-6)}$;
- R$_5$' is alkyl$_{(C1-12)}$, substituted alkyl$_{(C1-12)}$, aryl$_{(C6-12)}$, or substituted aryl$_{(C6-12)}$; or is taken together with R$_6$' and is alkanediyl$_{(C1-6)}$ or substituted alkanediyl$_{(C16)}$;
- R$_6$ is alkyl$_{(C1-12)}$, substituted alkyl$_{(C1-12)}$, aryl$_{(C6-12)}$, or substituted aryl$_{(C6-12)}$; is taken together with R$_5$ and is alkanediyl$_{(C1-6)}$ or substituted alkanediyl$_{(C1-6)}$; or is taken together with R$_6$' and is alkanediyl$_{(C1-6)}$ or substituted alkanediyl$_{(C1-6)}$; and
- R$_6$' is alkyl$_{(C1-12)}$, substituted alkyl$_{(C1-12)}$, aryl$_{(C6-12)}$, or substituted aryl$_{(C6-12)}$; is taken together with R$_5$' and is alkanediyl$_{(C1-6)}$ or substituted alkanediyl$_{(C1-6)}$; or is taken together with R$_6$ and is alkanediyl$_{(C1-6)}$ or substituted alkanediyl$_{(C1-6)}$.

13. The method of claim 12, wherein the diphosphine ligand is further defined as:

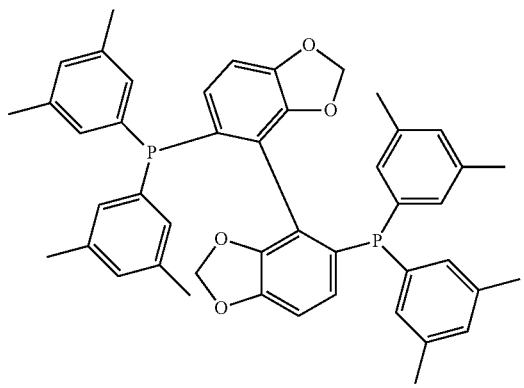

14. The method of claim 1, wherein the catalyst is present in the product mixture in an amount from about 10 ppm to about 1,000 ppm.

15. The method of claim 1, wherein the reaction time of step (ii) is from about 0.5 hours to about 4 hours.

16. The method of claim 1, wherein the method results in an HMPA yield greater than 50%.

17. The method of claim 1, wherein the method results in an allyl alcohol conversion percentage of greater than 75%.

18. A method comprising:
(i) admixing an α-olefin$_{(C3-24)}$ selected from hexene, allyl alcohol, allyl acetate and vinyl acetate, a substituted α-olefin$_{(C3-24)}$, or styrene with CO and H$_2$ to form a starting material mixture; and
(ii) reacting the starting material mixture in the presence of a catalyst under conditions capable of producing linear and branched aldehydes,
wherein the catalyst is a transition metal complex comprising a transition metal ion and a diphosphine ligand with a bite angle from about 70° to about 100°, and wherein the ratio of the linear to branched aldehydes is less than 1.5:1.

19. The method of claim 18, wherein the diphosphine ligand is further defined as:

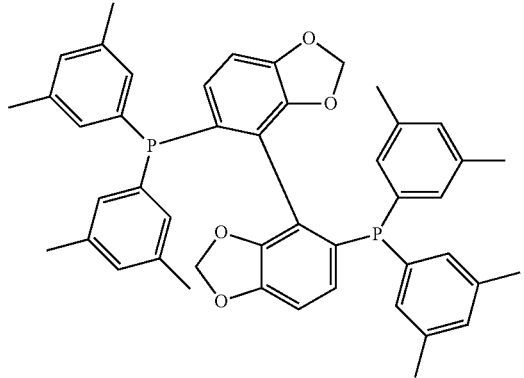

* * * * *

UNITED STATES PATENT AND TRADEMARK OFFICE
CERTIFICATE OF CORRECTION

PATENT NO. : 9,790,156 B2
APPLICATION NO. : 15/340389
DATED : October 17, 2017
INVENTOR(S) : Daniel F. White et al.

Page 1 of 1

It is certified that error appears in the above-identified patent and that said Letters Patent is hereby corrected as shown below:

In the Claims

Column 17    Line 38    In Claim 12, delete "$R_6$'" and insert --$R_6$--
Column 17    Line 42    In Claim 12, delete "alkanediyl$_{(C16)}$;" and insert --alkanediyl$_{(C1-6)}$--

Signed and Sealed this
Tenth Day of March, 2020

Andrei Iancu
*Director of the United States Patent and Trademark Office*